(12) United States Patent
Bradley et al.

(10) Patent No.: US 7,449,757 B2
(45) Date of Patent: Nov. 11, 2008

(54) NANOSTRUCTURES WITH ELECTRODEPOSITED NANOPARTICLES

(75) Inventors: Keith Bradley, New York, NY (US); Alona J. Davis, San Francisco, CA (US); Jean-Christophe P. Gabriel, Pinole, CA (US); Tzong-Ru Han, El Cerrito, CA (US); Vikram Joshi, San Francisco, CA (US); Alexander Star, Albany, CA (US)

(73) Assignee: Nanomix, Inc., Emeryville, CA (US)

( * ) Notice: Subject to any disclaimer, the term of this patent is extended or adjusted under 35 U.S.C. 154(b) by 0 days.

(21) Appl. No.: 10/945,803

(22) Filed: Sep. 20, 2004

(65) Prior Publication Data

US 2005/0157445 A1  Jul. 21, 2005

Related U.S. Application Data

(60) Provisional application No. 60/504,663, filed on Sep. 18, 2003.

(51) Int. Cl.
*G01N 27/403* (2006.01)
(52) U.S. Cl. ...................................... 257/414; 977/720
(58) Field of Classification Search ................ 977/720, 977/721, 723; 257/414; 361/226
See application file for complete search history.

(56) References Cited

U.S. PATENT DOCUMENTS

| | | | |
|---|---|---|---|
| 4,851,195 A | 7/1989 | Matthews et al. | |
| 5,246,859 A | 9/1993 | Nelson et al. | |
| 5,382,417 A | 1/1995 | Haase | |
| 5,827,997 A * | 10/1998 | Chung et al. | ................ 174/388 |
| 6,217,828 B1 | 4/2001 | Bretscher et al. | |
| 6,465,132 B1 | 10/2002 | Jin | |
| 6,489,394 B1 | 12/2002 | Andros | |
| 6,797,325 B2 | 9/2004 | Wang et al. | |
| 2002/0130333 A1 * | 9/2002 | Watanabe et al. | ........... 257/200 |
| 2003/0041438 A1 | 3/2003 | Wei et al. | |
| 2003/0180640 A1 * | 9/2003 | Darty | .......................... 430/31 |
| 2004/0018587 A1 | 1/2004 | Makowski et al. | |
| 2004/0023428 A1 | 2/2004 | Gole et al. | |
| 2004/0029297 A1 * | 2/2004 | Bonnell et al. | ................. 438/3 |
| 2004/0091285 A1 | 5/2004 | Lewis | |
| 2004/0104129 A1 * | 6/2004 | Gu et al. | ..................... 205/775 |
| 2004/0120183 A1 | 6/2004 | Appenzeller et al. | |
| 2004/0158410 A1 | 8/2004 | Ono et al. | |
| 2004/0188780 A1 * | 9/2004 | Kurtz | ......................... 257/414 |
| 2004/0211580 A1 * | 10/2004 | Wang et al. | ............ 174/35 MS |
| 2005/0072213 A1 * | 4/2005 | Besnard et al. | ............ 73/31.06 |
| 2005/0112052 A1 * | 5/2005 | Gu et al. | .................. 423/447.1 |

FOREIGN PATENT DOCUMENTS

WO   WO200215240 A *  2/2002  ................... 438/3

\* cited by examiner

*Primary Examiner*—Thomas L Dickey
(74) *Attorney, Agent, or Firm*—Weaver Austin Villeneuve & Samspson LLP

(57) ABSTRACT

A nanoelectronic device includes a nanostructure, such as a nanotube or network of nanotubes, disposed on a substrate. Nanoparticles are disposed on or adjacent to the nanostructure so as to operatively effect the electrical properties of the nanostructure. The nanoparticles may be composed of metals, metal oxides, or salts, and nanoparticles composed of different materials may be present. The amount of nanoparticles may be controlled to preserve semiconductive properties of the nanostructure, and the substrate immediately adjacent to the nanostructure may remain substantially free of nanoparticles. A method for fabricating the device includes electrodeposition of the nanoparticles using one or more solutions of dissolved ions while providing an electric current to the nanostructures but not to the surrounding substrate.

12 Claims, 7 Drawing Sheets

NANOSTRUCTURES WITH ELECTRODEPOSITED NANOPARTICLES

CROSS-REFERENCE TO RELATED APPLICATION

This application claims priority pursuant to 35 U.S.C. § 119(e) to U.S. Provisional Application No. 60/504,663, filed Sep. 18, 2003, which application is specifically incorporated herein, in its entirety, by reference.

BACKGROUND OF THE INVENTION

1. Field of the Invention

The present invention relates to electrical devices using nanostructures, for example, nanotubes or nanowires, as a conductive element.

2. Description of Related Art

Electronic devices using nanostructures as electrical conductors are useful as transistors, optoelectronic devices, and chemical and biological sensors. Nanostructures that have been used in such devices include carbon nanotubes and silicon nanowires. For a variety of reasons, it is desirable to modify the nanostructures. Modified nanostructures can have improved electrical characteristics, greater sensitivity to chemicals, or greater specificity in their sensitivity to chemicals. However, these modifications can be difficult to effect. Some modifications have been made to nanostructures in solution, before they have been incorporated into a device. This approach is limited to those nanostructures which can be readily put into solution.

Nanostructures on substrates have been modified by the addition of metal. Specifically, physical vapor deposition has been used to produce thin films of metal on the substrates on which the nanostructures are disposed. As a result, the nanostructures are also coated with solid metal. By careful choice of the deposition conditions, the metal can be induced to form into nanoparticles. These particles coat the substrate and the nanostructures uniformly, which may be undesirable for some applications. Lithography can be used to restrict the formation of the particles to defined regions. But the minimum size of these regions is limited by the techniques of lithography, and within these regions the particle coatings are uniform.

A exemplary problem arises by the incorporation of nanotubes into electronic devices for use as hydrogen sensors. Nanotube electronic devices which operate as transistors can be coated with palladium to enhance their sensitivity to hydrogen. However, the uniformity of the coating within lithographically-definable regions of minimum size prevents the electronic devices from operating as transistor-type sensors. The nanoparticle coating is too conductive relative to the semiconducting nanostructure. If the palladium coating could be deposited on the nanoscale architecture of the sensor device in a more controlled fashion, the characteristic transistor properties could be preserved. It should be apparent that this problem is not limited to the deposition of palladium onto nanotubes devices, and may be encountered in any nanoscale electronic device for which it is desired to selectively deposit nanoparticles of a material on or adjacent to a nanostructure, such as a semiconducting nanostructure.

It is desirable, therefore, to better control the deposition of nanoparticles, such as metallic nanoparticles, onto selected regions of a nanoelectronic device. For example, it is desirable to deposit nanoparticles of different types on different regions of a nanoelectronic device. In addition, it would be desirable to provide nanoelectronic devices that take advantage of greater control over nanoparticle deposition.

SUMMARY OF THE INVENTION

The invention provides electronic devices comprising nanostructures on substrates with nanoparticles deposited in a controlled pattern over the substrate and nanostructures. The deposition pattern may comprise features that are too fine to be defined using conventional lithography, for example, individual nanostructures may be deposited with nanoparticles while immediately adjoining regions of the substrate are not. The nanoparticles may comprise the same material, or different materials. Different nanoparticle materials may be deposited in succession, or at approximately the same time.

According to an embodiment of the invention, nanoparticles are deposited by electrodeposition from a solution covering the nanostructures, which are already disposed on a substrate. By controlling the parameters of the electrodeposition process, materials in the solution may be caused to deposit as nanoparticles primarily on the nanostructures, or generally in contact with the nanostructures. Different materials may be deposited from the same solution, or from a succession of different solutions.

The geometry of the nanostructures in the nanoelectronic devices on the substrate may be used to create different types of deposition patterns. For example, in an embodiment of the invention, nanoparticles with different chemical compositions may be caused to form clusters of nanoparticles at particular locations on the nanostructures. In the alternative, or in addition, different materials may be deposited in nanoparticles having a layered structure, with each layer comprising a different material. A further variation is to form nanoparticles of different materials in different regions of a nanostructure film or other structure. Since all of the materials can be localized to the nanostructures using a method according to the invention, the substrate may remain substantially unaffected by deposition of the nanoparticles.

Electrodeposition of the nanoparticles may enable a high degree of control and versatility with respect to the materials being deposited. Embodiments of the invention include structures with nanoparticles of metals, metal oxides, and salts. For example, embodiments may include nanoparticles of Ag, Au, Ir, Ni, Os, Pd, Pt, Rh, and Ru. Nanostructure embodiments include individual nanostructures and nanostructure networks or matrices. For example, a nanostructure film comprising a nanotube network of multiple individual carbon nanotubes may be advantageous, such as described in U.S. application Ser. No. 10/177,929, filed Jun. 21, 2002, which is incorporated by reference herein.

The invention is not limited to any particular type of device, and may be adapted for use with a variety of different nanoelectronic devices. Such devices may include, for example, transistors (incorporating a third electrode, the gate electrode); a diode; a logic element; a circuit; a resistor; a chemical or biological sensor; modified to be an n-type, p-type, or ambipolar transistor; a light-emitting diode; or a physical sensor (e.g. light or pressure).

The invention further provides a method for manufacture of the nanostructure devices with multiple nanoparticle coatings. First, an electronic device incorporating a nanostructure disposed on a nonconductive substrate is prepared. In one example, nanostructures are drop cast on substrates with previously prepared electrodes. In another example, nanostructures are grown on a substrate by chemical vapor deposition. After the nanostructures are disposed on the substrate, metal electrodes are deposited by physical vapor deposition and lithographically patterned. Various other methods for forming electrodes may also be used, as known the art.

Second, the nanoelectronic device is connected via any suitable electrical contact to a source of current. The source may permit the magnitude of the current or supplied voltage to be controlled. Reagent solutions are prepared which include the materials to be deposited. The reagent solutions contain ions which can be electrochemically reduced to yield solids of the desired materials. Embodiments include solutions of metal salts, including metal chlorides.

The electronic device is exposed to the reagent solutions in the sequence in which the nanoparticles are to be deposited. The same nanostructure region of the device may be exposed to the same sequence of reagents. In the alternative, different nanostructure regions, for example, regions connecting different sets of electrodes, may be exposed to different reagents or different reagent sequences. For each solution, current source is controlled to permit current flow through the nanostructure in the electronic device.

The quality of the nanoparticle deposition may be controlled by controlling the magnitude and duration of the current flow while the device is immersed in the reagent solution. For example, if both current flow and reagent solution are present for a long time, large particles of material are deposited on any conductive surface in contact with the solution. This may include the electrical contacts of the electronic device and the nanostructure itself. Accordingly, the conjunction of current flow and the presence of reagent solution is restricted to a brief period of time. For example, the duration of the current flow may restricted to a period less than 90 seconds while in contact with the reagent, for a specified current. Other parameters that may be controlled include the properties of the reagent solution, such as the concentration of ions in solution. Control may be accomplished in various ways; for example, by limiting the current source to permit current flow only during a brief period of time, or by removing the reagent solution from the nanoelectronic device after a brief period of time. After the deposition of a first type of nanoparticle, a second type of nanoparticle may be deposited by exposing the nanostructures to a second reagent solution and permitting current flow.

Further control of deposition patterns may be accomplished by controlling current flow through portions of a device. For example, a device may be provided with distinct regions defined by one or more electrical contacts. Current may be caused to flow only to a desired region or regions of the device by controlling the voltages of the electrodes that define the region. Electrodeposition can thereby be caused to occur in a selected portion of the device. For further example, a nanostructure network may be configured such that current is highest at nodes of the nanostructure. Nanoparticles may be selectively deposited at the nodes by stopping the electrodeposition process after nanoparticles are deposited primarily at the nodes.

A more complete understanding of the nanostructure with electrodeposited nanoparticles, and methods for making it, will be afforded to those skilled in the art, as well as a realization of additional advantages and objects thereof, by a consideration of the following detailed description of the preferred embodiment. Reference will be made to the appended sheets of drawings which will first be described briefly.

DETAILED DESCRIPTION OF THE PREFERRED EMBODIMENT

The present invention provides a nanostructure device with electrodeposited nanoparticles, and method for making it, that overcome limitations of the prior art. In the detailed description that follows, like element numerals are used to describe like elements that appear in one or more of the figures.

Figure 1:
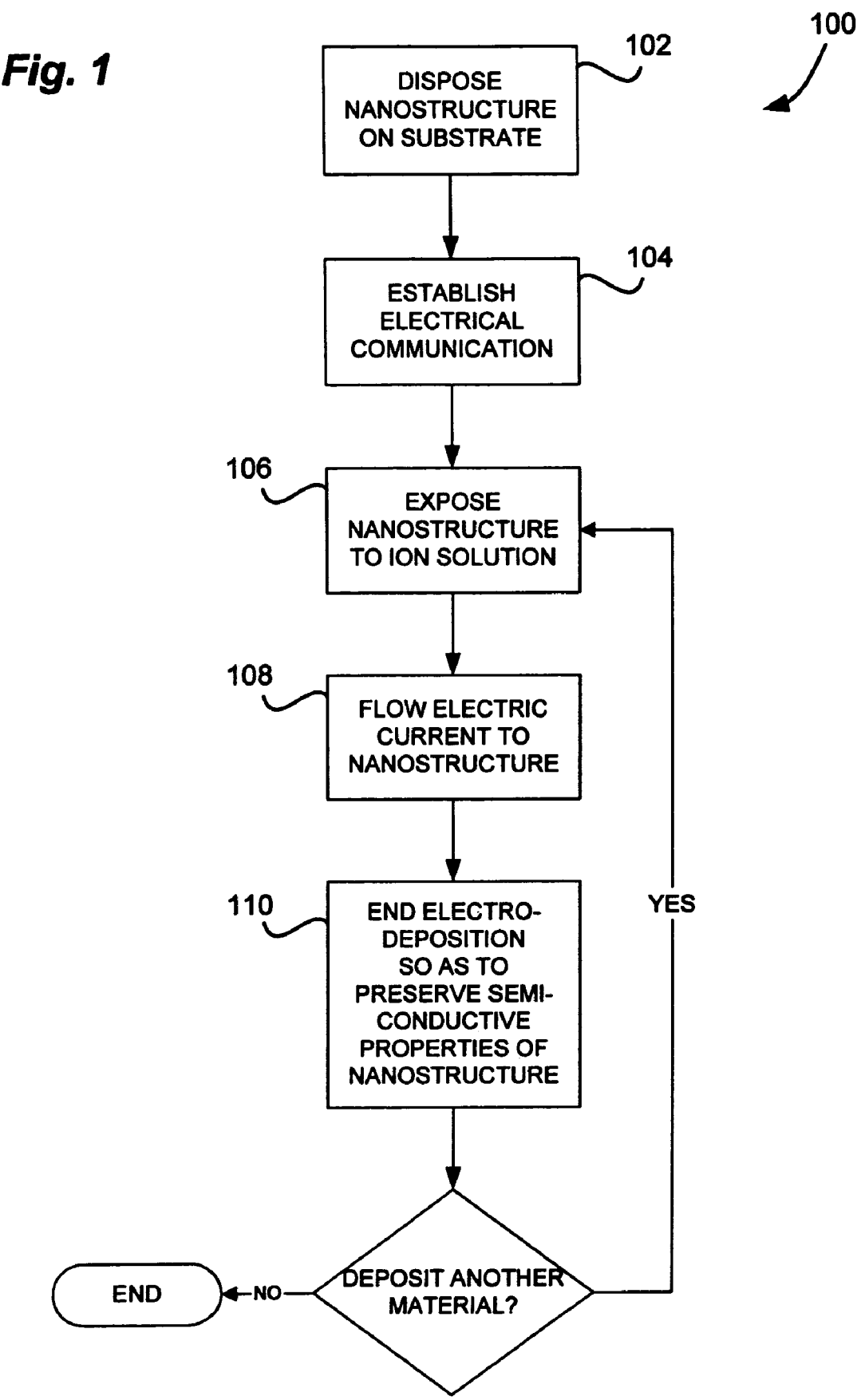
FIG. 1 is a flow chart showing exemplary steps of a method for making a nanoelectronic device according to the invention.
Figure 3:
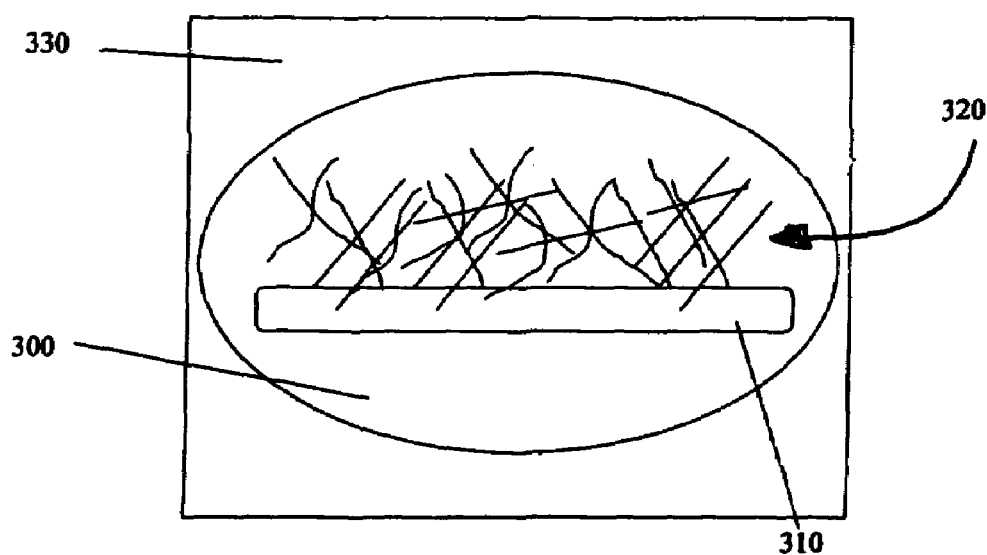
FIG. 3 is a simplified plan view of the materials shown in FIG. 2.
Figure 4:
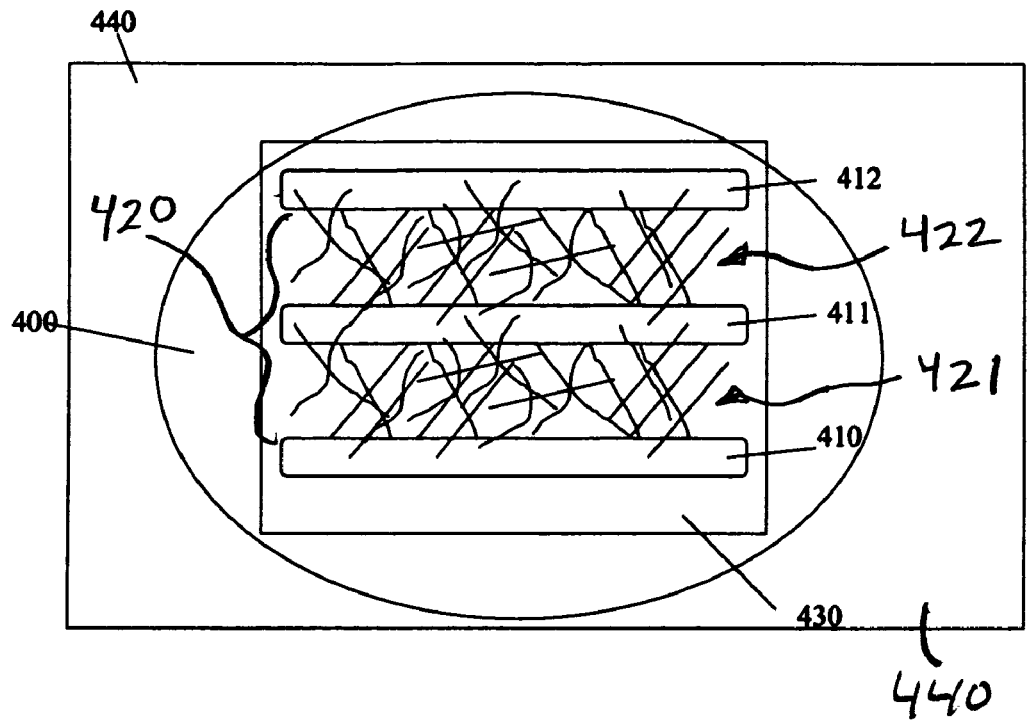
FIG. 4 is a simplified plan view showing an alternative arrangement of materials during electrodeposition.

Exemplary steps of a method 100 for making an nanostructure with deposited nanoparticles are shown in FIG. 1. According to an initial step 102 of the method, a nanostructure is disposed on a substrate. Any suitable method may be used. For many devices, nanostructure films are believed advantageous. A suitable method for disposing a nanostructure film is disclosed in U.S. application Ser. No. 10/177,929. Such films may comprise a plurality of randomly oriented nanotubes lying substantially parallel to the substrate surface. FIGS. 3 and 4 show a schematic plan view of nanotube films 320, 420 over substrates 330, 430.

In addition to nanotube films, films or other arrangements of other nanostructures, including individual nanostructures, can be used. Alternative nanostructures may include, for example, nanospheres, nanocages, nanococoons, nanofibers, nanowires, nanoropes and nanorods. Such alternative nanostructures may be adapted similarly to nanotubes for the embodiments described herein. Nanostructures can be made of many different elements and compounds. Examples include carbon, boron, boron nitride, and carbon boron nitride, silicon, germanium, gallium nitride, zinc oxide, indium phosphide, molybdenum disulphide, and silver.

Substrates for the devices include rigid substrates and flexible substrates. Examples of rigid substrates include silicon substrates, silicon oxide substrates, silicon nitride substrates, and aluminum oxide substrates. Examples of flexible substrates include polymer substrates. The substrate material should be generally non-conductive at the surface supporting the device.

Figure 2:
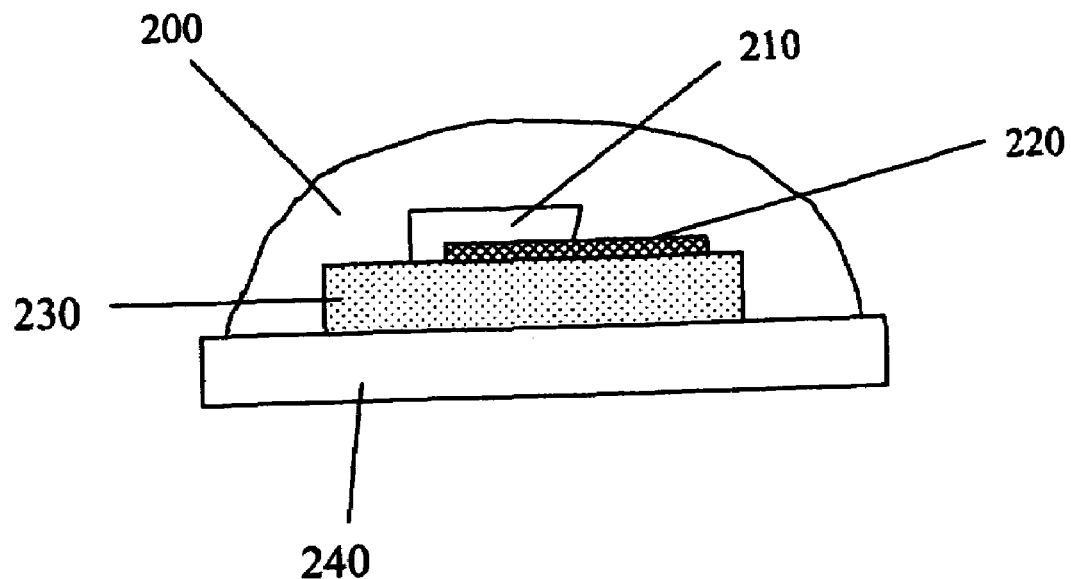
FIG. 2 is a simplified enlarged side view showing an exemplary arrangement of materials during an electrodeposition step of the invention.

Referring again to FIG. 1, at step 105 electrical communication is established with the nanostructure. The electrical connection should be suitable for providing an electrodeposition current to the nanostructure. For lithographically fabricated devices, an electrical connection to the nanostructure may be provided via a metallic contact 210 patterned on the substrate 230 surface, as shown in FIG. 2. FIG. 3 shows a contact 310 in electrical communication with a nanotube film 320 along its length. More than one contact may be used, as shown in FIG. 4, wherein contacts 410, 411, 412 divide nanostructure 420 into regions 421, 422. Contacts as shown in FIGS. 2-3 may later be used as electrodes of a nanotube device incorporating the nanostructure with electrodeposited nanoparticles. It should be apparent that any desired number of nanotube devices may be provided on a single substrate, for example, for later use as a multi-analyte sensor, or for mass production on large substrates.

Methods for patterning contacts on substrates are known in the art, and any suitable method may be used. Electrical contacts may be patterned on the substrate before or after nanostructures are patterned on the substrate. Nanostructure films may be deposited over a pattern of contacts and etched away in areas between the devices under fabrication. Another method may be to form individual or multiple nanostructures between contacts; such electrical contacts may comprise a catalyst material for nanotube formation. Details for formation or deposition of nanostructures over or in a pattern of electrical contacts on a substrate are known in the art, and any suitable method may be used.

Referring again to method 100 of FIG. 1, at step 106, the nanostructure may be exposed to a ions of a material to be deposited dissolved in a suitable solvent. The solvent should not react with the nanostructure. The solution should have a composition such that nanoparticles of a desired composition may be electrochemically reduced to yield solids of the desired materials. For example, dissolved metals, metal ions, or various salt solutions may be used. More specifically, embodiments include solutions of metal salts, including metal chlorides. For example, solutions of Na2RhCl6, HAuCl4, Na2PtCl4, Na2PdCl4, RuCl3, RhCl3, NiCl2, AgCl, PdCl2, OsCl3, and IrCl3 may be suitable. Suitable solvents may include water and various organic solvents, or mixtures thereof. Solutions of the foregoing salts in water and ethanol at a concentration level of about 5 mM are believed to be useful, but the invention is not limited to any particular solvent or concentration level.

At step 108, an electric current is caused to flow through the nanostructure into the surrounding solution. For example, an voltage difference may be maintained between an electrical contact to the nanostructure and the surrounding solution. Referring to FIG. 2, contact 210 may be maintained at a first voltage by connection to a suitable source, while the solution 200 is grounded via conductive base plate 240. Device substrate 230 is non-conductive. Thus, electrodeposition from the solution may be caused to occur on contact 210 and nanostructure 220, but not on the substrate 230.

FIG. 3 shows elements similar to FIG. 2, but in plan view. When current is caused to flow into the solution from contact 310 and its electrically connected nanotube network 320, electrodeposition of ions from solution 300 can be caused to occur on network 320 and not on the surrounding non-conductive substrate 330.

The amount of material electrodeposited from solution should be controlled so as to deposit a desired quantity of material in nanoparticle form on or adjacent to the nanostructures. As shown in FIG. 1 at step 110, control may generally be accomplished by ending the electrodeposition process soon enough to preserve the semiconductive properties of the nanostructure. To stop electrodeposition, either the reagent solution may be removed, the current supplied to the nanostructure may be shut off, or both. The proper period for electrodeposition will differ depending on the details of the device being constructed. It may be helpful to monitor electrical properties of the device being electrodeposited, for example its conductivity, to help ensure that the quantity of material deposited does not exceed a desired threshold.

Current flow need not necessarily be provided by application of an external power source through electrical contacts to the nanostructure. For example, current flow through the nanostructure may be provided by means of electrolytic oxidation of a metal on the substrate, with the metal in electrical communication with the nanostructures. To control the period of time during which current flow and exposure to reagent solution are conjoined, the solution may be removed after a period of time.

Different materials may be deposited by repeating steps 104-110 for each different material. The different materials may be deposited in different regions of a nanostructure, or in substantially the same region. FIG. 4 shows a configuration for depositing different materials in different regions 421, 422 of a nanostructure 420. The regions are divided by contact 411 and bounded on opposite ends by contacts 410, 412. The nanostructure is immersed in a reagent solution 400 and supported by a non-conductive substrate 430. A conductive base plate 440 serves to ground the solution 400.

Each region 421, 422 may be connected to a current source by a distinct one of contacts 410, 412. The regions are separated and defined by an additional contact 411. In a first deposition cycle, nanoparticles are deposited in a first region 421 by permitting current flow through the electrical contact 410 in the first region while a first reagent solution is present. To prevent deposition in a second region, the electrical contact 411 separating the first and second regions is connected to a source of electrical voltage. This voltage source controls the voltage between this electrical contact and the reagent solution, by means of a contact placed in the first solution. The voltage between the contact and the first solution is selected to prevent electrodeposition of material from the first solution. As a result, nanoparticles are deposited only on the nanostructures in the first region. In a subsequent second deposition cycle, nanoparticles are deposited in the second region 422 by permitting current flow through the electrical contact 412 in the second region while a second reagent solution is present. Meanwhile, the electrical contact separating the first and second regions continues to be maintained at a voltage selected to prevent electrodeposition of material from the second solution.

Figure 5A:
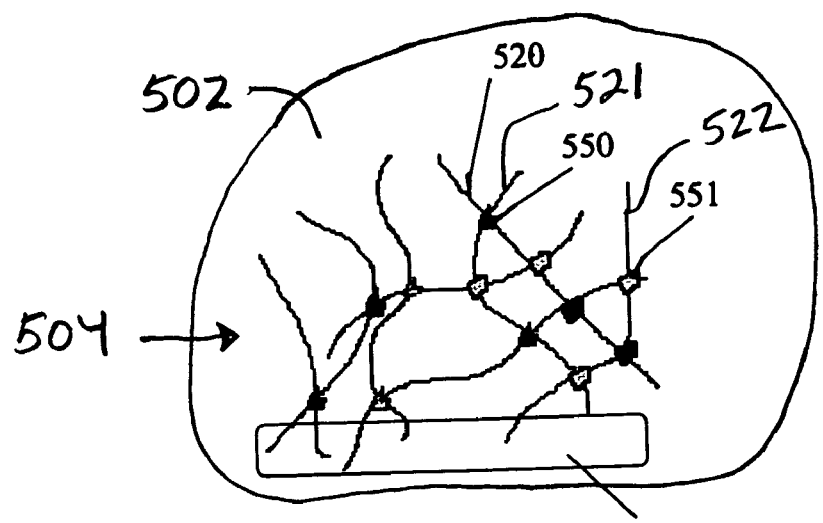
FIGS. 5A-5C are schematic diagrams showing various different arrangements of nanoparticles in operative association with an adjacent nanostructure.
Figure 5B:
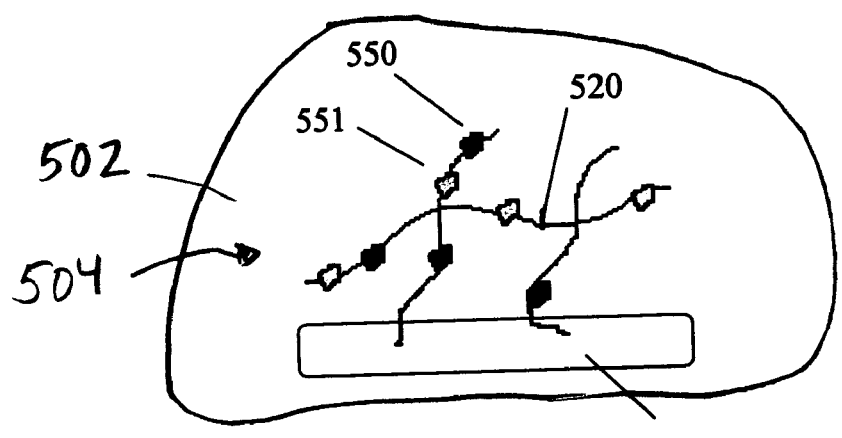
Figure 5C:
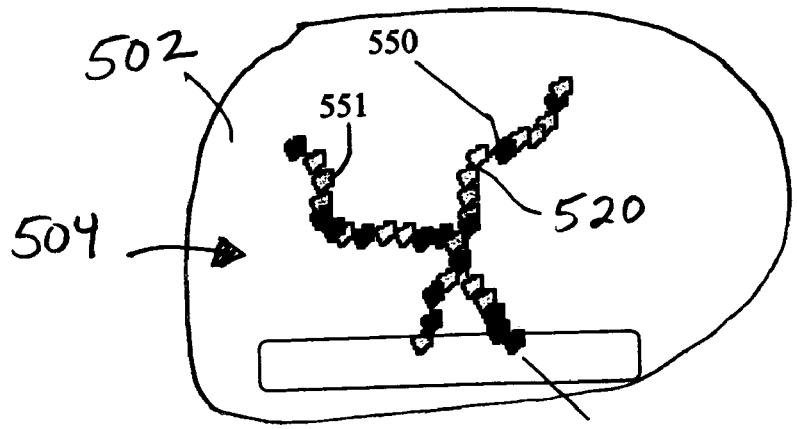

Different materials may also be deposited so as to be localized in the same nanostructure. FIGS. 5A-C show different exemplary embodiments. In FIG. 5A, contact 510 is in electrical communication with nanotube network 504 on substrate 502. Nanoparticles of different materials are deposited on different nodes of the network. For example, a nanoparticle of a first material 550 is deposited at the node between nanotubes 520 and 521, while a nanoparticle of a second material 551 is deposited at the node between nanotube 522 and 520. A structure such as shown in FIG. 5A may be formed by stopping electrodeposition after about half of the nodes of network 504 have been deposited with material from a first solution. The process then may be continued with a second solution until the remaining nodes are occupied. This assumes electrodeposition will occur more robustly at the nodes of a network than elsewhere, so that nanoparticles are first deposited at the nodes.

FIG. 5B shows a variation similar to that shown in 5A, except that deposition at the nodes does not occur more robustly than elsewhere. In this embodiment, the different nanoparticles 550, 551 are randomly distributed across the network 504. FIG. 5C shows the same topography as 5B, but with a denser deposition of nanoparticles.

Figure 6A:
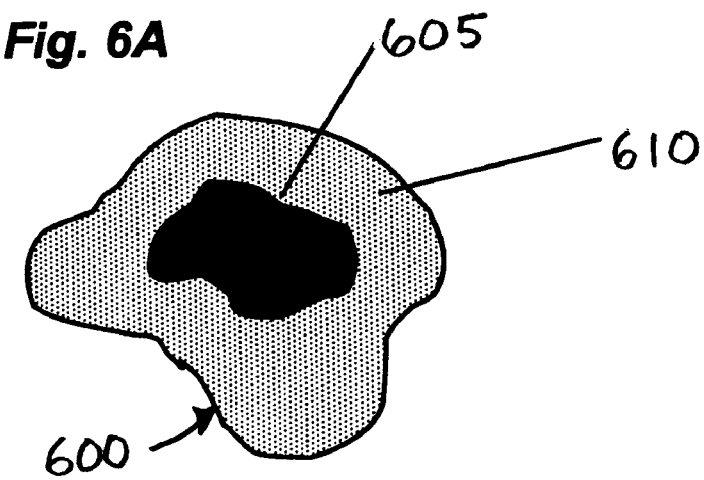
FIG. 6A shows an exemplary nanoparticle composed of different material layers.
Figure 6B:
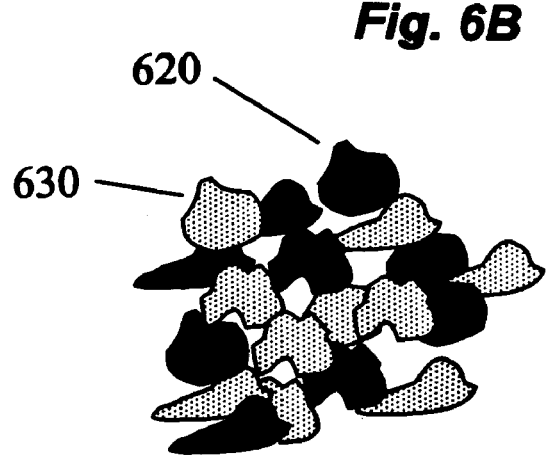
FIG. 6B shows a cluster of nanoparticles of composed of different materials.

Nanoparticles may also be formed having a layered construction, as shown in FIG. 6. Nanoparticle 600 has a core 605 of a first material and a shell 610 of a second material. Another possibility is formation of a cluster of nanoparticles, with nanoparticles of different type 620, 630 distributed through the cluster.

EXAMPLE 1

A nanotube network was prepared as described in U.S. application Ser. No. 10/177,929. A titanium film was deposited by evaporation and patterned lithographically into the form of electrical contacts. The substrate was placed on an aluminum block, this block being electrically grounded. Copper and iron blocks were also used for some experiments. Metal pins were pushed onto several of the titanium contacts on the substrate, thus making electrical contact. These metal pins were electrically grounded. The chip was rinsed with a 1:1 mixture of water and ethanol for cleaning. A 5 mM solution of $PdCl_2$ in a 1:1 mixture of water and ethanol was prepared. Five drops of the solution were placed on the substrate, with the solution contacting both the substrate and the underlying aluminum block. After 30 seconds, the solution was rinsed off with a 1:1 mixture of water and ethanol, and the chip was dried with a stream of compressed air. Subsequently, a 5 mM solution of $Na_3RhCl_6$ in a 1:1 mixture of water and ethanol was prepared. Five drops of the solution were placed on the substrate, with the solution contacting both the substrate and the underlying aluminum block. After 30 seconds, the solution was rinsed off with a 1:1 mixture of water and ethanol, and the chip was dried with a stream of compressed air.

Figure 7:
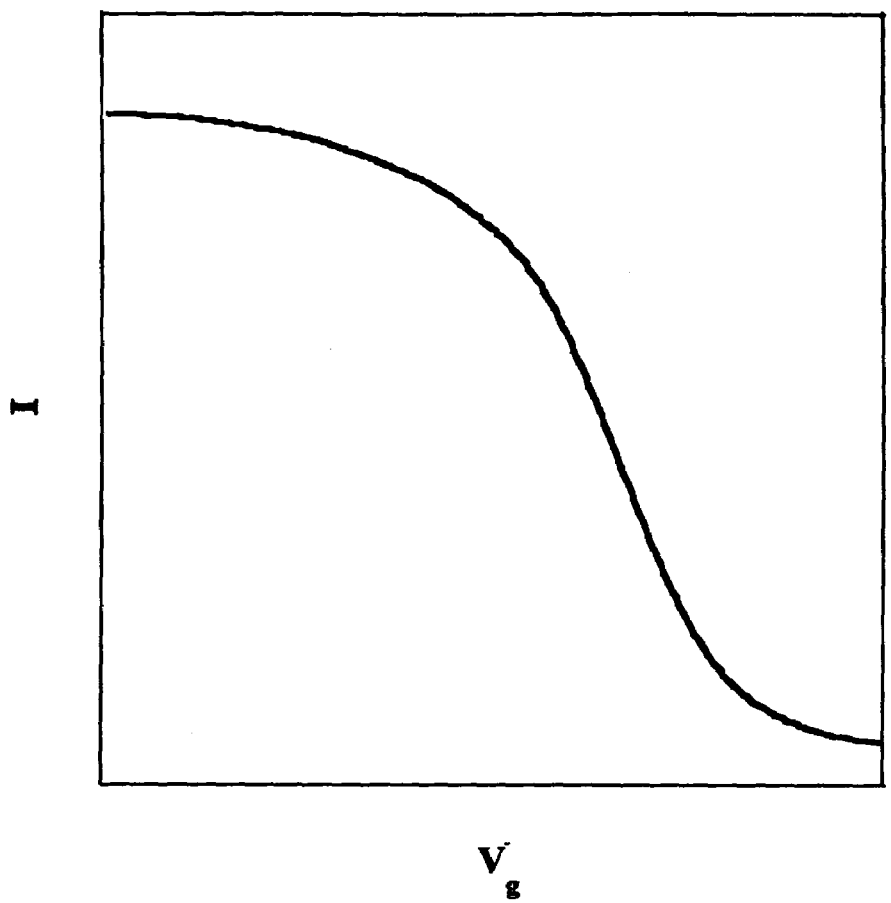
FIG. 7 is a chart illustrating an exemplary electrical property of a device according to the invention.

The resulting device was characterized electrically. FIG. 7 is illustrative of a transfer characteristic for a device like that of Example 1, which illustrates that it behaves as a transistor. That is, the curve shows dependency of the current on gate voltage. Transistor operation is retained because the nanoparticles are specifically deposited on the nanostructures.

Figure 8:
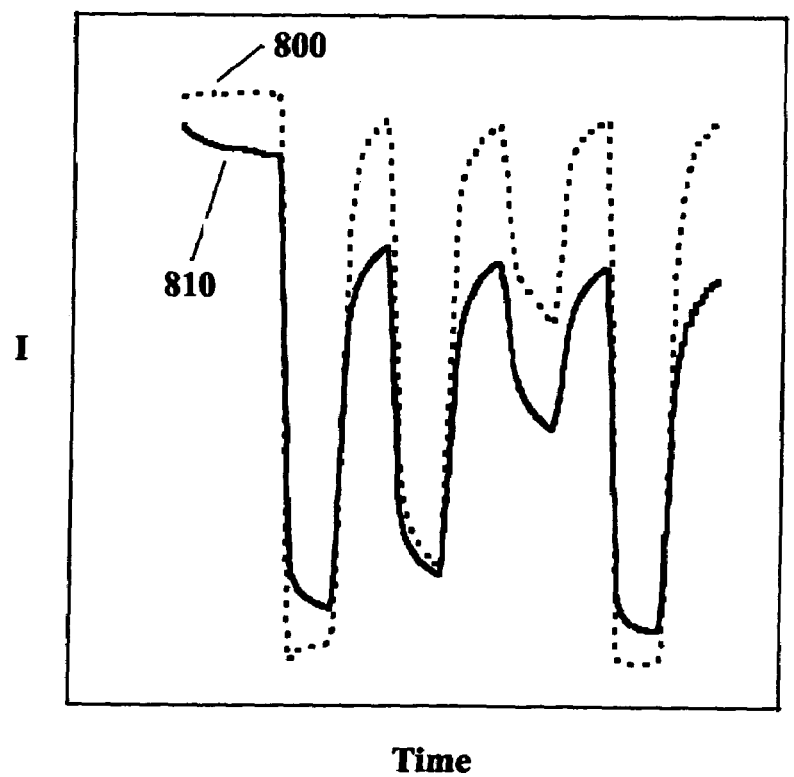
FIG. 8 is a chart showing an exemplary response of a nanoelectronic gas sensor device according to the invention.

FIG. 8 shows the operation of a device prepared as in Example 1 as a hydrogen sensor. A device prepared as in Example 1 was cycled between hydrogen in air and pure air. Curve 800 shows the response over time in humid air. Curve 810 shows the response over time in dry air. Comparison of curves 800, 810 leads to the conclusion that the device responds more strongly to hydrogen in humid air, but is useful as a hydrogen sensor in both dry and humid air.

EXAMPLE 2

A nanotube network was prepared like that of Example 1. An aluminum (or other possible counterelectrode metal) film (50 nm) was deposited by evaporation and patterned lithographically into the form of electrical contacts. The chip was rinsed with a 1:1 mixture of water and ethanol for cleaning. The chip was then submerged in a vial of ~1 mL 5 mM PdCl2 solution in a 1:1 mixture of water and ethanol. After 30 seconds, the chip was removed from the vial and the solution was rinsed off with a 1:1 mixture of water and ethanol. Finally, the chip was dried with a stream of compressed air. Subsequently, a 5 mM solution of $Na_3RhCl_6$ in a 1:1 mixture of water and ethanol was prepared. The chip was then submerged in ~1 mL of the $Na_3RhCl_6$ solution. After 30 seconds, the solution was rinsed off with a 1:1 mixture of water and ethanol, and the chip was dried with a stream of compressed air.

EXAMPLE 3

Application of an electrodeposition process to fabrication of multi-analyte sensor arrays was demonstrated. The finished sensor arrays were tested by passing different analytes over the sensor array and resolving signatures for the given gases, thereby identifying them. In a laboratory setting, various gases were delivered to the surface of the sensor array. Response data was collected and analyzed using a technique for negate the bias associated with poisoning and nonrandom sampling. The data stream was then filtered and processed through principal component analysis (PCA) to recognize the signature associated with each gas analyte.

Site-specific metal electrodeposition was used to deposit nanoparticles of different composition on different regions of nanotube films in adjacent sensor devices on a chip. Adjacent devices were thereby functionalized to respond to different analytes. Control of the electrodeposition process was accomplished by grounding specific nanotube devices on the chip.

Figure 9:
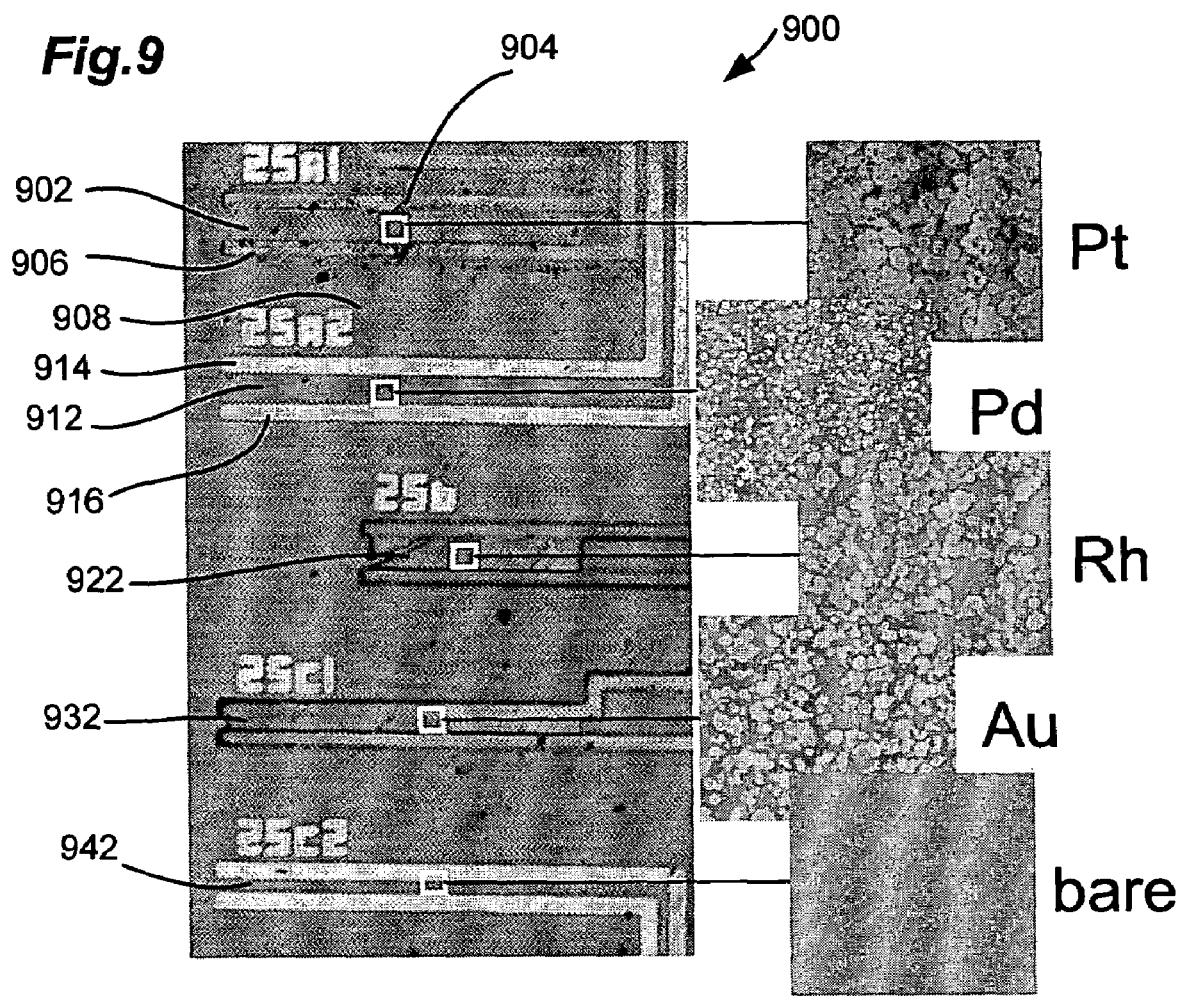
FIG. 9 is a plan view of an exemplary multi-analyte sensor array according to an embodiment of the invention.

FIG. 9 shows an exemplary multi-analyte sensor chip 900 prepared according to example 3. Five different regions are apparent. At the top of the figure, a region 902 is deposited with Pt nanoparticles between electrodes 904, 906. An area of the substrate 908 that is substantially free of electrodes separates region 902 from an adjacent region 912. Region 912 lies between electrodes 914, 916, and is deposited with Pd nanoparticles. Chip 900 also includes an Rh-deposited region 922, an Au-deposited region 932, and a bare (undeposited) region 942. The nanostructure for every region on chip 900 is a nanotube network.

To fabricate a chip like that shown in FIG. 9, a nanotube transistor chip was prepared having multiple nanotube network field-effect transistor (NTNFET) devices. Each NTNFET included a nanotube film like that prepared for Examples 1 and 2, disposed between opposing titanium/gold electrodes acting as source and drain. A third electrode was disposed in the substrate near the nanotube network film as a gate electrode. The nanotube transistor chip was placed on an aluminum block, and the block was electrically grounded. Metal pins were pushed onto two of the titanium/gold contacts on the nanotube chip related to a single NTNFET device, thus making electrical contact. These metal pins were electrically grounded. The chip was rinsed with a 1:1 mixture of water and ethanol for cleaning. A 5 mM solution of $PdCl_2$ in a 1:1 mixture of water and ethanol was prepared. Five drops of the solution were placed on the substrate, with the solution contacting both the substrate and the underlying aluminum block. After 30 seconds, the solution was rinsed off with a 1:1 mixture of water and ethanol, and the chip was dried with a stream of compressed air. This process was repeated for additional devices on the nanotube chip. The following 5 mM metal salt solutions ($Na_3RhCl_6$, $Na_2PtCl_4$, $HAuCl_4$) in a 1:1 mixture of water and ethanol were used on subsequent devices to functionalize with Rh, Pt, and Au, respectively.

The sensor array was connected to a measurement circuit and exposed to five different test gases, with five exposures for each different gas, as shown in Table 1 below. The order of tests was randomized to separate the desired signal from the possible effects of drift and poisoning of the sensors and any changes in the gas delivery system. A single test consisted of a five-minute settling period, five-minute exposure to gas followed by a ten-minute recovery period. I-$V_G$ measurements were taken continuously with gate voltage sweep frequency of 2 Hz and amplitude of 9V.

TABLE 1

Test Conditions

| Test gas | P, ppm |
|---|---|
| CO | 2500 |
| $H_2$ | 10000 |
| $H_2S$ | 50 |
| $NH_3$ | 200 |
| $NO_2$ | 5 |

Test Sequence:
CO, $H_2$, $NH_3$, $H_2$, $H_2S$, $NO_2$, $NO_2$, $NO_2$, $H_2$, $H_2$, $NO_2$, $H_2S$, $NH_3$, $NH_3$, $H_2$, $H_2S$, $H_2S$, CO, $NO_2$, CO, $H_2S$, $NH_3$, CO, $NH_3$, CO The measurement data was analyzed using Principle Component Analysis (PCA). This method allows one to represent most of the variance in fewer dimensions. An ordered orthogonal basis is calculated, where the first basis vector corresponds to the largest variance in the original data, the second to the second largest variance and so on. Each measurement channel provides an original vector.

Figure 10A:
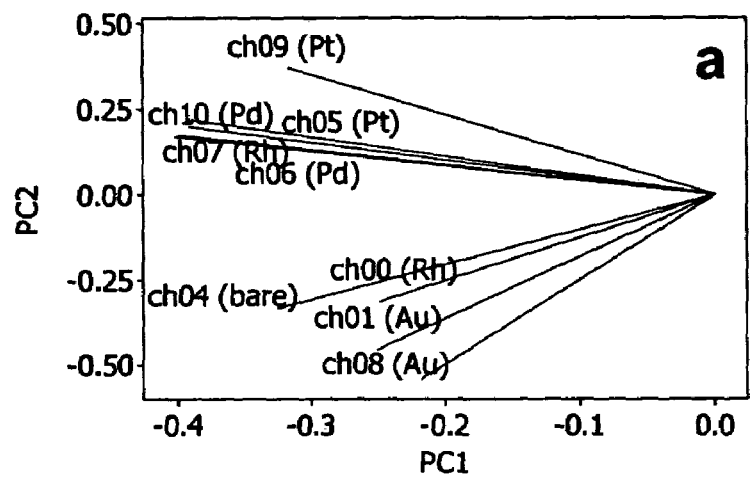
FIGS. 10A-10C are charts illustrating results of a principal component analysis for the sensor array of the type shown in FIG. 9.
Figure 10B:
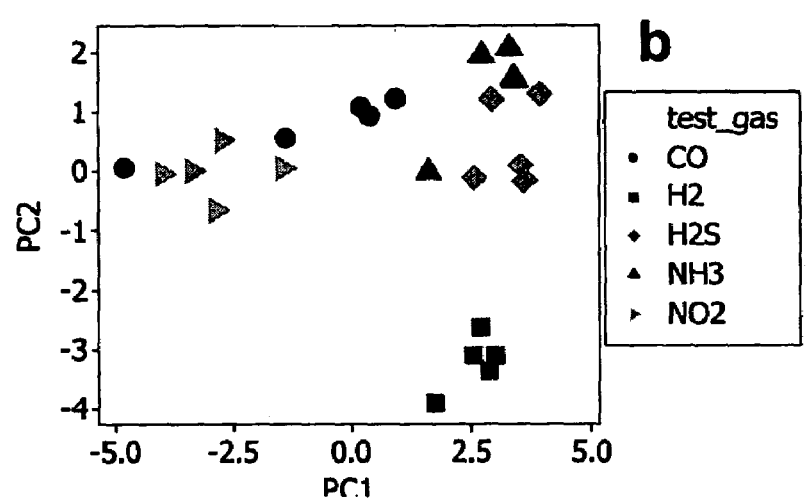
Figure 10C:
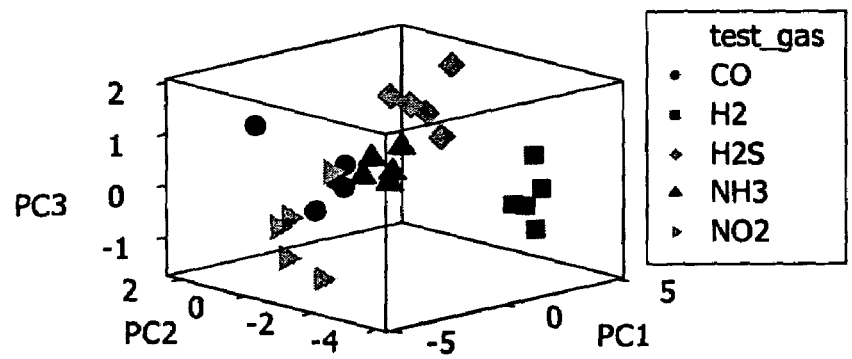

FIG. 10A shows the loadings (coefficients) used to rotate the data, and indicate the relative importance of the original vectors. The scores on the vertical and horizontal axes represent the position of the data points in the new vector space. Typically, the scores for the first two components are plotted. However, in this example, the third component is still relatively important. The two- and three-dimensional plots of scores are shown in FIGS. 10B, 10C, respectively. The points corresponding to each five analytes are clustered in separate regions of the space of the first three principal components, demonstrating the effectiveness of the multi-analyte sensor.

Having thus described a preferred embodiment of nanostructures with electrodeposited nanoparticles, and methods of making them, it should be apparent to those skilled in the art that certain advantages of the within system have been achieved. It should also be appreciated that various modifications, adaptations, and alternative embodiments thereof may be made within the scope and spirit of the present invention. For example, specific examples have been illustrated for nanotube film nanostructures, but it should be apparent that the inventive concepts described above would be equally applicable to other types of nanostructures. The invention is further defined by the following claims.

What is claimed is:

1. An electronic device, comprising: a substrate; a film disposed over the substrate, the film comprising at least two nanostructures and divided into at least two distinct regions by at least one electrode; at least one first nanoparticle operatively associated with the film in a first region of the at least two distinct regions; at least one second nanoparticle operatively associated with the film in a second region of the at least two distinct regions, wherein at least one of the first nanoparticle and the second nanoparticle comprises a metal oxide.

2. The device of claim 1, wherein the second nanoparticle has a substantially different composition from the first nanoparticle.

3. The device of claim 1, further comprising a gate electrode electrically isolated from the film.

4. The device of claim 1, wherein the film is further divided by at least one film-free region.

5. The device of claim 1, wherein at least one of the first nanoparticle and the second nanoparticle are disposed on the film.

6. The device of claim 1 further comprising at least one contact in electrical communication with the first region of the film.

7. An electronic device, comprising: a substrate; a film disposed over the substrate, the film comprising at least two nanostructures and divided into at least two distinct regions by at least one electrode; at least one first nanoparticle operatively associated with the film in a first region of the at least two distinct regions; at least one second nanoparticle operatively associated with the film in a second region of the at least two distinct regions, wherein at least one of the first nanoparticle and the second nanoparticle comprises a salt.

8. The device of claim 7, wherein the second nanoparticle has a substantially different composition from the first nanoparticle.

9. The device of claim 7, further comprising a gate electrode electrically isolated from the film.

10. The device of claim 7, wherein the film is further divided by at least one film-free region.

11. The device of claim 7, wherein at least one of the first nanoparticle and the second nanoparticle are disposed on the film.

12. The device of claim 7, further comprising at least one contact in electrical communication with the first region of the film.

* * * * *